United States Patent [19]

Pilgram et al.

[11] Patent Number: 4,500,345
[45] Date of Patent: Feb. 19, 1985

[54] ISOXAZOLOTRIAZINDIONES AND PLANT GROWTH INHIBITING USE THEREOF

[75] Inventors: Kurt H. Pilgram; Thomas P. Price, both of Modesto, Calif.

[73] Assignee: Shell Oil Company, Houston, Tex.

[21] Appl. No.: 553,020

[22] Filed: Nov. 18, 1983

[51] Int. Cl.³ .................. A01N 31/08; C07D 498/04
[52] U.S. Cl. .......................................... 71/93; 544/223
[58] Field of Search ............... 544/223, 220; 424/249; 71/93, 90

[56] References Cited

U.S. PATENT DOCUMENTS 3,719,676  3/1973  Crank .................................. 544/223

OTHER PUBLICATIONS

Kayama et al., C.A., vol. 84, 1976, p. 519, 84:59402v.

*Primary Examiner*—Henry R. Jiles
*Assistant Examiner*—J. G. Mullins

[57] ABSTRACT

Certain isoxazolotriazinediones, useful for controlling the growth of unwanted plants.

6 Claims, No Drawings

ISOXAZOLOTRIAZINDIONES AND PLANT GROWTH INHIBITING USE THEREOF

DESCRIPTION OF THE INVENTION

It has been found that the growth of certain plants is adversely affected by isoxazolotriazinediones of the formula:

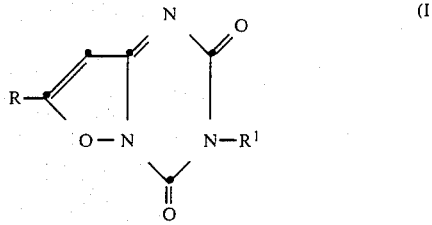

wherein R is alkyl of one to six carbon atoms, alkynyl of three to six carbon atoms, cyclopropyl or 1-methylcyclopropyl, and $R^1$ is alkyl or alkoxy of from one to four carbon atoms, and hydrohalide salts thereof.

In these compounds, each alkyl, alkoxy and alkynyl moiety suitable is either straight-chain or branched-chain in configuration. Highest toxicity with respect to plants appears to occur when the moiety R is 1,1-dimethylethyl.

Compounds of Formula I can be prepared by treating a solution of the appropriate urea

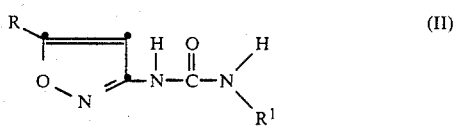

in an inert solvent with phosgene. The reaction proceeds according to the equation:

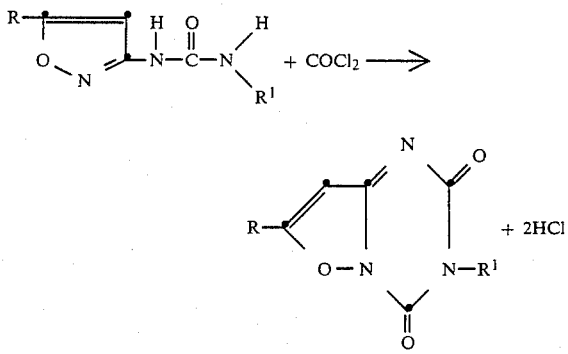

The treatment is conveniently conducted by slowly adding a solution of the urea in an inert solvent to a stirred solution of phosgene in the same solvent, at a low temperature, for example, about −20° C. or lower, then heating the stirred mixture at a moderately high temperature, for example, 60° C. to 90° C., for a period of time sufficient to ensure completion of the reaction. As is shown in the examples set out hereinafter, a suitable solvent is ethyl acetate. The desired products are isolated from the crude product by conventional means, as illustrated in the examples.

The urea precursors are a known class of compounds, being described, and methods for their preparation being described, in U.S. Pat. No. 4,062,861 and British Pat. No. 2,079,283. British Pat. No. 2,014,992 describes the amine precursor for the urea in which the moiety R is 1,1-dimethylethyl; other amine precursors can be prepared by methods disclosed in that patent.

The preparation, isolation and testing of two typical individual species of the compounds of Formula I are described in the examples, following. The class of compounds is further illustrated and exemplified by the following further individual species, all of which are specifically contemplated in this invention. In the interest of brevity, in the identification of these species, they are identified in terms of the substituent moieties, Formula I:

| Species No. | R | $R^1$ |
|---|---|---|
| 1 | 1,1-dimethyl-2-propynyl | methyl |
| 2 | 1,1-dimethyl-2-butynyl | methyl |
| 3 | 1-methylcyclopropyl | methyl |
| 4 | 1,1-dimethylpropyl | methyl |
| 5 | 1,1-dimethylethyl | 2-propynyl |
| 6 | 1,1-dimethylethyl | 2-butynyl |

The urea precursor for Species No. 1 has been prepared in a particular instance as follows:

The methyl ester of 2,2-dimethyl-3-butynoic acid (A) was prepared from the acid (M. A. Schexnayder and P. S. Engel, Journal of the American Chemical Society, Vol. 97, pp 4825 et seq. (1975)) by conventional procedures.

A mixture of 109.8 g of A and 56.2 g of acetonitrile was added drop-by-drop to a stirred, refluxing mixture of 72.5 g of sodium hydride and 650 ml of tetrahydrofuran. The resulting mixture was stirred and refluxed for 2 hours, then cooled to 20° C. and stirred for 18 hours. Then the solvent was evaporated in a rotary evaporator, the residue was drowned in 500 ml of ether, and water was added cautiously. The resulting aqueous phase was separated, acidified with hydrochloric acid and extracted with ether. The extract was dried (MgSO$_4$) and the solvent was evaporated. The residue, a dark viscous syrup, was distilled to give ((1,1-dimethyl-2-propyn-1-yl)carbonyl)acetonitrile (B), a yellow liquid, b.p.: 65°-67° C. (0.5 Torr.).

Over a 15-minute period, 21.0 g of B was added to a solution of 15.8 g of hydroxylamine hydrochloride and 9.1 g of sodium hydroxide in 240 ml of water and 200 ml of ethanol at room temperature. The pH of the mixture was adjusted to 6.4–6.6. The mixture was stirred, heated to 90° C. and stirred at that temperature for 8 hours. The ethanol was evaporated under reduced pressure and the aqueous residue, cooled to room temperature, was extracted with ether. The extract was dried (MgSO$_4$) and concentrated. The resulting amber syrup was chromatographed over silica gel, using a 2:15:33 v:v:v mixture of tetrahydrofuran, ethyl acetate and hexane as eluent, to give 3-amino-5-(1,1-dimethyl-2-propynyl)-isoxazole (C), as an off-white solid, m.p.: 98°-100° C.

A solution of 7.5 g of C and 5 ml of methyl isocyanate in 50 ml of tetrahydrofuran was heated at 50°-60° C. for two days. The solvent was evaporated under reduced pressure and the residue was chromatographed over silica gel, using as eluent a 1:4:20 v:v:v mixture of tetrahydrofuran, ethyl acetate and hexane, to give 1-methyl- 3-(5-(1,1-dimethyl-2-propynyl)-isoxazol-3-yl)urea, as a white crystalline solid, m.p.: 99°–100° C.

As for Species No. 2, the precursor ester has been prepared in a particular instance as follows:

A flask was immersed in a dry ice/acetone mixture. It was charged with 500 ml of liquid ammonia and 30.2 g of sodium amide was added. The internal temperature of the stirred mixture was controlled at −45° C.–50° C. for 30 minutes, then a solution of 110.1 g of methyl iodide in 100 ml of ether was added drop-by-drop (45 minutes). The stirred mixture then was allowed to warm to room temperature and was stirred for four hours, then 200 ml of ether and 200 ml of cold water were added, the resulting mixture was stirred, and the two liquid phases were allowed to separate. The ether phase was concentrated under reduced pressure to give the methyl ester of 2,2-dimethyl-3-pentynoic acid, as a dark syrup. The ester can be converted to the urea precursor by the procedures described for converting A to the urea precursor for Species No. 1.

The urea precursor for Species No. 3 has been prepared as follows:

A mixture of 61.1 g of acetonitrile and 108.3 g of methyl 1-methylcyclopropanecarboxylate was added drop-by-drop over a one-hour period to a stirred, refluxing mixture of 35.8 g of sodium hydride and 650 ml of tetrahydrofuran. The resulting mixture was stirred and refluxed for a further 18 hours, then most of the solvent was evaporated in a rotary evaporator. The residue was dissolved in 1 liter of water, and the solution was acidified with hydrochloric acid and extracted with ether. The extract was dried (MgSO$_4$) and concentrated. The residue, a liquid, was fractionally distilled to give (1-methylcyclopropylcarbonyl)acetonitrile (D) as a colorless oil which crystallized on standing, m.p.: 32°–33° C.

D was converted to 3-amino-5-(1-methylcyclopropyl)-isoxazole (E), a white solid, m.p.: 82°–84° C., by the method and procedures described in U.S. Pat. No. 4,062,861.

A solution of 1.0 g of E and 0.6 g of methyl isocyanate in 15 ml of ether containing one drop of triethylamine was held at 22° C. for 18 hours. Then the mixture was cooled to −10° C. and filtered, giving 1-methyl-3-(5-(1-methylcyclopropyl)-isoxazol-3-yl)urea, as a colorless solid, m.p.: 144°–147° C.

The urea precursor for Species No. 4 can be prepared from methyl 2,2-dimethylbutanoate by the procedures described in British Pat. No. 2,014,992.

Species Nos. 5 and 6 can be prepared from 3-isocyanato-5-(1,1-dimethylethyl)isoxazole (Compound 3, Example 3, hereinafter) and propargylamine, and 2-butynylamine, respectively.

In preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1

7-(1,1-dimethylethyl)-3-methyl-2H-isoxazolo-[2,3a]-(1,3,5)-triazine-2,4(3H)-dione hydrochloride (1)

A solution of 41.5 g of hydroxylamine hydrochloride in 136 ml of water was added drop-by-drop over a 10-minute period to a stirred, refluxing mixture of 56.1 g of pivaloylacetonitrile (British Pat. No. 2,014,992), 700 ml of water and 525 ml of ethanol. The mixture was held under those conditions for 7 hours, the pH of the mixture being periodically adjusted to 6.5 by the addition of either hydrogen chloride or aqueous sodium hydroxide solution, as required. Then the solvent ethanol was evaporated in a rotary evaporator, and the residual liquid was dried (MgSO$_4$), dissolved in 200 ml of hexane and chilled. Filtration gave 3-amino-5-(1,1-dimethylethyl)-isoxazole (1A), a yellow solid, m.p.: 107°–109° C.

1A was converted to (1-methyl-3-(5-(1,1-dimethylethyl)-isoxazol-3-yl)urea (1B) by the method and procedures disclosed in U.S. Pat. No. 4,062,861.

A 1000 ml flask was charged with 250 ml of ethyl acetate. Via a sparger, 14.9 g of phosgene was introduced into the stirred ester. Then a solution of 10.0 g of 1B in 380 ml of ethyl acetate was added drop-by-drop to the stirred ester/phosgene mixture, held at a temperature below −10° C. The stirred mixture then was heated to reflux (78° C.) for one hour and forty-five minutes, filtered, and the solid was dried, to give 1, as a colorless solid. m.p.: 223°–225° C. (with decomposition).

EXAMPLE 2

The free base of 1, i.e., 2, was prepared as follows:

5 g of 1 was taken up in 100 ml of water and 100 ml of ether. The mixture was made basic with ammonium hydroxide and extracted with ether. The extract was dried (MgSO$_4$) and concentrated to near dryness. Hexane was added, the mixture was cooled and filtered, to give 2, as a colorless solid, m.p.: 211°–213° C.

EXAMPLE 3

7-(1,1-dimethylethyl)-3-methoxy-2H-isoxazolo-[2,3a]-(1,3,5-)-triazine-2,4(3H)-dione (3)

99 g of phosgene was dissolved in 500 ml of ethyl acetate, then a solution of 71.6 g of 1A in 400 ml of ethyl acetate was added drop-by-drop to the stirred mixture. The mixture was stirred at reflux temperature for five hours, left standing overnight at room temperature, and filtered. The solid was dried at room temperature for two days to give dimeric 3-isocyanato-5-(1,1-dimethylethyl)-isoxazole (3A) m.p.: 165°–167° C.

8.5 g of methoxyamine was added slowly to a stirred solution of 15 g of 3A in 600 ml of tetrahydrfuran. The resulting mixture was filtered and the solid was triturated with ether to give 1-methoxy-3-(5-(1,1-dimethylethyl)-isoxazol-3-yl)urea (3B), m.p.: 145°–148° C.

3B was treated with phosgene according to the procedure described for 1B in Example 1, to give an oil. The oil was chromatographed over silica gel using as eluent a 1:1:2 v:v:v mixture of tetrahydrofuran, ethyl acetate and hexane, to give two fractions, each a solid. Both were recrystallized from ether/hexane. The second fraction was 3, a colorless solid, m.p.: 160°–163° C.

EXAMPLE 4

7-(1,1-dimethylethyl)-3-(1-methylethyl)-2H-isoxazolo-[2,3a](1,3,5-)triazine-2,4(3H)-dione (4)

7.5 g of 1-methylethyl isocyanate was added to a stirred mixture of 6.2 g of 1A and 75 ml of tetrahydrofuran at room temperature, then the mixture was stirred at reflux temperature for 24 hours, when an additional 7.5 g of 1-methylethyl isocyanate was added and the mixture was stirred at reflux temperature for 24 hours. The mixture was concentrated to dryness to give a syrup.

On standing overnight at room temperature, a solid formed. The solid was recrystallized from ether/hexane to give 1-(1-methylethyl)-3-(5-(1,1-dimethylethyl)-isoxazol-3-yl)urea (4A), as an off-white solid, m.p.: 135°–138° C.

5.9 g of phosgene was dissolved in 300 ml of ethyl acetate. Then, at 5° C., a solution of 6.7 g of 4A in 100 ml of ethyl acetate was added drop-by-drop. Then the mixture was stirred and heated at reflux for 50 minutes, and concentrated. The cooled residue was mixed with water and ether, and the mixture was made basic with ammonium hydroxide and extracted with ether. The extract was washed with water, dried ($MgSO_4$) and concentrated to near-dryness. Hexane was added, the mixture was cooled and filtered to give 4, as an off-white solid, m.p.: 167°–170° C.

Compounds of Formula I have been found to affect adversely the growth of plants, many of which are commonly considered as weeds, and therefore to be useful for controlling the growth of such unwanted plants. Compounds of Formula I have been found to have selectivity with respect to some crop plants—i.e., they control weeds at dosages at which they do not significantly harm the crop plants. Compounds of Formula I appear to be effective when applied preemergence or preplant incorporated (applied to the soil before the seeds have sprouted) or when applied postemergence (applied to the foliage of the growing plant). Some appear to be somewhat more effective when applied preemergence than when applied postemergence. Some appear to be more active with respect to broadleaved plants than with respect to grasses.

Accordingly, the invention includes a method of combatting unwanted plants which comprises applying to the locus an effective amount of a compound of Formula I. In the cases where it is desired to control weeds in crop plantings, it is of course preferable to employ the lowest dosage that will control the weeds, for this will minimize any possible deleterious effect of the compound upon the crop plants. For application, the compound generally is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:
Barnyardgrass (watergrass)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnson grass—*Sorghum halepense*
Morningglory—*Ipomoea purpurea* L. (Roth)

TEST PROCEDURES

The preemergence (soil) herbicidal activity of the compounds was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of the invention was evaluated by spraying 10-day-old crabgrass plants, 13-day-old pigweed plants, 6-day-old Johnsongrass plants, 9-day-old velvetleaf plants, 9-day-old yellow foxtail plants and either 9-day-old sicklepod plants or 5-day-old morningglory plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of 0.025% solution (about one pound of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | |
| --- | --- | --- | --- | --- | --- | --- | --- | --- | --- | --- | --- | --- |
| | Preemergence | | | | | | Postemergence | | | | | |
| Compound | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| 1 | 9 | 9 | 8 | 9 | 7 | 9 | 3 | 8 | 0 | 6 | 0 | 8 |
| 2 | 9 | 9 | 2 | 7 | 0 | 4* | 5 | 9 | 3 | 6 | 0 | 3* |
| 3 | 8 | 8 | 0 | 5 | 3 | 6 | 5 | 9 | 2 | 2 | 0 | 5 |

TABLE I-continued

| | HERBICIDAL ACTIVITY | | | | | | | | | | | |
|---|---|---|---|---|---|---|---|---|---|---|---|---|
| | Preemergence | | | | | | Postemergence | | | | | |
| Compound | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| 4 | 4 | 6 | 0 | 2 | 0 | 2* | 3 | 4 | 0 | 0 | 0 | 0* |

*These values were for morningglory.

EXAMPLES OF SELECTIVITY

In the following examples, the species of plants that were tested were:
Barnyardgrass
Downy Brome
Johnsongrass
Wild oats—*Avena fatua*
Yellow foxtail
Goose grass—*Eleusine indica L.*
Yellow nutsedge—*Cyperus esculentus L.*
Cocklebur—*Xanthum pennsylvanicum*
Morning glory
Wild mustard—*Brassica kaber*
Redroot pigweed
Sicklepod
Velvetleaf
Corn—*Zea mays*
Cotton—*Gossypium hirsutum*
Rice—*Oryza sativa*
Grain sorghum—*Sorghum vulgare*
Soybeans—*Glycine max*
Sugarbeets—*Beta vulgaris*
Wheat—*Triticum aestivum*

TEST PROCEDURES

The preemergence activity of Compound (1) was further determined with respect to certain species of crop plants and common species of weeds, by spraying a formulation of the test compound on soil in small pots in which seeds of the plants had been sown. The results of the tests were evaluated on the basis of the 0–9 scale described with respect to the earlier tests. The results of the tests are reported in Table II.

TABLE II

| | COMPOUND 1 | | | |
|---|---|---|---|---|
| | Rating of Effect at Indicated Dosage (lb/acre) | | | |
| | Preemergence | | Postemergence | |
| Plant Species | 0.25 | 1.0 | 0.25 | 1.0 |
| Corn | 0 | 0 | 0 | 0 |
| Cotton | 2 | 3 | 3 | 4 |
| Rice | 4 | 9 | 2 | 3 |
| Grain Sorghum | 0 | 3 | 0 | 4 |
| Soybean | 5 | 9 | 6 | 7 |
| Sugar Beet | 8 | 9 | 6 | 6 |
| Wheat | 2 | 7 | 0 | 0 |
| Barnyard Grass | 0 | 6 | 0 | 0 |
| Downy Brome | 3 | 9 | 0 | 0 |
| Johnsongrass | 0 | 3 | 0 | 0 |
| Wild Oats | 3 | 9 | 0 | 0 |
| Yellow Foxtail | 0 | 3 | 0 | 0 |
| Goose Grass | 4 | 5 | 0 | 0 |
| Yellow Nutsedge | 0 | 0 | 0 | 0 |
| Cocklebur | 5 | 9 | 4 | 6 |
| Morning Glory | 3 | 9 | 4 | 5 |
| Mustard | 8 | 9 | 2 | 3 |
| Pigweed | 9 | 9 | 6 | 7 |
| Sicklepod | 6 | 9 | 5 | 9 |
| Velvetleaf | 6 | 9 | 7 | 7 |
| Nightshade | — | — | 3 | 6 |

We claim:

1. A compound of the formula

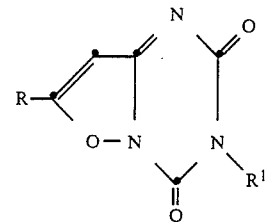

wherein R is alkyl of one to six carbon atoms, alkynyl of three to six carbon atoms, cyclopropyl or 1-methylcyclopropyl, an $R^1$ is alkyl or alkoxy of from one to four carbon atoms, and the hydrohalide salts thereof.

2. A compound according to claim 1 wherein R is 1,1-dimethylethyl, $R^1$ is methyl.

3. A method for inhibiting the growth of unwanted plants at a locus which comprises applying to the locus a plant growth inhibiting effective amount of a compound of claim 1.

4. A method for inhibiting the growth of unwanted plants at a locus which comprises applying to the locus a plant growth inhibiting effective amount of a compound of claim 2.

5. A plant growth inhibiting composition which comprises a plant growth inhibiting effective amount of a compound of claim 1 and an inert carrier, a surface-active agent, or both.

6. A composition according to claim 5 wherein R is 1,1-dimethylethyl and $R^1$ is methyl.

* * * * *